(12) United States Patent
Hayashi et al.

(10) Patent No.: US 7,214,313 B2
(45) Date of Patent: May 8, 2007

(54) LIQUID CHROMATOGRAPH

(75) Inventors: Morimasa Hayashi, Ashiya (JP); Yosuke Iwata, Kyoto (JP); Yusuke Osaka, Mino (JP)

(73) Assignee: Shimadzu Corporation, Kyoto (JP)

( * ) Notice: Subject to any disclaimer, the term of this patent is extended or adjusted under 35 U.S.C. 154(b) by 286 days.

(21) Appl. No.: 11/088,930

(22) Filed: Mar. 25, 2005

(65) Prior Publication Data
US 2005/0218055 A1 Oct. 6, 2005

(30) Foreign Application Priority Data
Mar. 30, 2004 (JP) .............................. 2004-097954

(51) Int. Cl.
*B01D 15/08* (2006.01)
(52) U.S. Cl. ...................... 210/198.2; 210/656; 422/70
(58) Field of Classification Search ................ 210/635, 210/656, 659, 198.2; 422/70; 96/101, 104
See application file for complete search history.

(56) References Cited

U.S. PATENT DOCUMENTS

| | | | |
|---|---|---|---|
| 4,597,943 A * | 7/1986 | Sugiyama et al. ............ 422/70 |
| 6,802,967 B2 * | 10/2004 | Masuda et al. .......... 210/198.2 |
| 6,942,793 B2 * | 9/2005 | Ito et al. ................... 210/198.2 |
| 6,955,760 B2 * | 10/2005 | Iwata ....................... 210/198.2 |
| 2003/0168392 A1 * | 9/2003 | Masuda et al. .......... 210/198.2 |
| 2004/0124128 A1 * | 7/2004 | Iwata ....................... 210/198.2 |
| 2004/0173509 A1 * | 9/2004 | Ito et al. ........................ 210/94 |
| 2006/0219638 A1 * | 10/2006 | Watanabe et al. ............ 210/656 |
| 2007/0023639 A1 * | 2/2007 | Yamashita et al. .......... 250/288 |

FOREIGN PATENT DOCUMENTS

JP 2003-254955 9/2003

OTHER PUBLICATIONS

Machine Language Translation of Japan Patent No. 2003-254955.*

* cited by examiner

*Primary Examiner*—Ernst G. Therkorn
(74) *Attorney, Agent, or Firm*—Manabu Kanesaka

(57) ABSTRACT

A two-dimensional liquid chromatograph includes a first-dimension separation channel for guiding a sample injected from a sample injection part to a first-dimension analysis column using a first-dimension analysis mobile phase for separation; two trap columns; an analysis channel for guiding components retained in the trap columns to a second-dimension analysis column using a second-dimension analysis mobile phase for analysis; and a channel switching mechanism. The switching mechanism connects the first-dimension separation channel to one of the trap columns and connecting the analysis channel to the other of the trap columns, and also switches connections between the trap columns and the channels.

5 Claims, 6 Drawing Sheets

LIQUID CHROMATOGRAPH

BACKGROUND OF THE INVENTION AND RELATED ART STATEMENT

The present invention relates to a liquid chromatograph such as a high-performance liquid chromatograph (HPLC). In particular, the present invention relates to a two-dimensional liquid chromatograph in which a first-dimension analysis column separates components and a trap column retains the components, and a second-dimension analysis column separates the components one more time.

A liquid chromatography includes various separation modes such as a normal phase, a reversed-phase, ion exchange, and size exclusion. A one-dimensional liquid chromatography uses one of the separation modes. It is sometimes difficult to analyze a sample with the one-dimensional liquid chromatography depending on a sample. For example, in a field of proteome analysis in which a biological sample is analyzed, when high-performance liquid chromatography is used to analyze components in one separation mode, a large number of eluted components are present, thereby overlapping peaks of the components. Accordingly, even when a mass spectrometer with high resolution is used as a detector, it is difficult to perform the analysis.

In order to solve the problem, a two-dimensional liquid chromatography capable of combining two separation modes with different mechanisms has been used. In the two-dimensional liquid chromatography, generally an ion exchange mode is used for separation according to ion strength as first-dimension separation, and components eluted from the ion exchange column are analyzed with a reversed-phase mode as second-dimension separation.

More specifically, an ion exchange column for the first-dimension separation and a reversed-phase column for the second-dimension separation are connected in series, and a detector is connected at a downstream side thereof. In the first-dimension separation, a mobile phase of the ion exchange mode flows in the ion exchange column for separating the components through a concentration gradient according to ion strength. In this case, only a part of the components is eluted and guided to the reversed-phase column. Then, the mobile phase is switched to the reversed-phase, and the part of the components eluted in the first-dimension is analyzed in the reversed-phase column while desalting as the second-dimension analysis to be detected by the detector. After the second-dimension separation and analysis, the mobile phase is switched again to the ion exchange mode to change the ion strength, so that the next eluted components are eluted through the first-dimension column. The mobile phase is switched again to the reversed-phase mode, and the desalting and second-dimension separation and analysis are performed.

Through the process, the two-dimensional liquid chromatography is performed by repeating the first-dimension separation and second-dimension separation. In the two-dimensional liquid chromatography, it takes a long period of time to replace the mobile phases in the system, thereby making it difficult to efficiently perform the analysis.

In order to solve the problem, a trap column has been provided. In this system, a first-dimension separation channel and a second-dimension separation channel are provided separately. After a component eluted from the first-dimension column is retained in the trap column, the channels are switched, and the component captured in the trap column is separated and analyzed by the second-dimension separation channel.

As compared with the system having two columns connected in series for the first-dimension and second-dimension separations, this system has an advantage in which a mobile phase liquid delivery pump for the first-dimension analysis in the ion exchange mode and a mobile phase liquid delivery pump for the second-dimension analysis in the reverse mode are provided separately, and the trap column is provided. When a part of the components is eluted at a certain concentration of ion strength and retained in the trap column in the first-dimension separation, the first-dimension mobile phase liquid delivery pump is stopped. Then, the channel switching valve connected to the trap column is switched, so that the second-dimension analysis is performed. When the second-dimension analysis is finished, the first-dimension pump is started again. Then, the concentration is changed, and the next eluted components are retained in the trap column. Then, the first-dimension pump is stopped, and the channel switching valve is switched, so that the second-dimension analysis is performed. By repeating the steps, the two-dimensional liquid chromatography is performed.

The system has an advantage in which the liquid delivery pumps for the respective mobile phases are separately provided, and the second-dimension analysis is performed in a state in which the component eluted in the first-dimension separation is concentrated. The system has a disadvantage in which it is necessary to stop the first-dimension liquid feed pump several times during the analysis, thereby lowering reproducibility. Further, the first-dimension analysis channel of the channel switching valve becomes an open system when the first-dimension separation is switched to the second-dimension analysis. Accordingly, the first-dimension mobile phase may leak from the first-dimension channel due to a residual internal pressure in the channel, thereby losing a component.

In order to solve the problem, a plurality of trap columns has been proposed (see Patent Document 1). In this system, all of the components are separated and eluted while applying a concentration gradient in the first-dimension separation, and all of the eluted components are retained by the plural trap columns. Then, the trap columns are successively connected to a channel for the second-dimension separation, thereby performing the second-dimension analysis. The system has an advantage in which the first-dimension separation is not interrupted during the analysis, thereby improving reproducibility of the analysis is good and eliminating leak of the components.

Patent Document 1: Japanese Patent Publication (Kokai) No. 2003-254955

In the method using the plural trap columns for retaining the eluted components separated in the first-dimension separation, it is possible to fractionate the components eluted in the first-dimension separation into only the number of the trap columns. However, when a sample contains a large number of components, it is necessary to provide a large number of trap columns, thereby increasing a size of an apparatus.

In view of the problems described above, an object of the present invention is to provide a two-dimensional liquid chromatograph capable of analyzing a large number of components with a minimum number of trap columns.

Further objects and advantages of the invention will be apparent from the following description of the invention.

SUMMARY OF THE INVENTION

In order to attain the objects described above, according to a first aspect of the present invention, a two-dimensional liquid chromatograph comprises: a first-dimension separation channel for guiding a sample injected from a sample injection part to a first-dimension analysis column using a first-dimension analysis mobile phase for separation; two trap columns; an analysis channel for guiding a component captured in the trap columns to a second-dimension analysis column using a second-dimension analysis mobile phase for analysis; and a channel switching mechanism for connecting the first-dimension separation channel to one of the trap columns and connecting the analysis channel, to the other of the trap columns, and also switching connections between the trap columns and the channels.

In the first aspect, it is preferable that a control device is provided for controlling the channel switching mechanism such that one of the trap columns is connected to the first-dimension separation channel for concentrating the separated component in a concentration operation and then the other of the trap columns is connected to the analysis channel in an eluting operation in this order, and the concentrating operation and the eluting operation are performed simultaneously.

In the first-dimension separation, the first-dimension analysis mobile phase sometimes contains a salt in order to perform optimal separation. When the salt remains in the second-dimension analysis, the second-dimension analysis mode may be negatively affected. When a mass spectrometer used as a detector in order to obtain high sensitivity and selectivity, if a salt enters the mass spectrometer, the salt may obstruct electro-spray ionization and movement of gasified ions to the mass spectrometer, thereby making it difficult to perform analysis under optimal conditions.

Therefore, desalting treatment may be performed before the second-dimension analysis. According to a second aspect of the present invention, a two-dimensional liquid chromatograph comprises: a first-dimension separation channel for guiding a sample injected from a sample injection part to a first-dimension analysis column using a first-dimension analysis mobile phase for separation; a plurality of trap columns; an analysis channel for guiding a component captured in the trap columns to a second-dimension analysis column using a second-dimension analysis mobile phase for analysis; a desalting mobile phase channel for supplying a desalting mobile phase; and a channel switching mechanism for connecting the first-dimension separation channel to one of the trap columns and connecting the analysis channel or the desalting mobile phase channel to another of the trap columns, and also switching connections between the trap columns and the channels.

In the second aspect, it is preferable that a control device is provided for controlling the channel switching mechanism such that one of the trap columns is connected to the first-dimension separation channel for concentrating the separated component in a concentration operation and then another of the trap columns is connected to the analysis channel in an eluting operation or to the desalting mobile phase channel in a desalting operation in this order, and the concentrating operation and the eluting operation or the desalting operation are performed simultaneously.

Further, it is preferable that three trap columns may be provided, and the control device controls the channel switching mechanism such that the concentrating operation, desalting operation, and eluting operation are performed simultaneously in different trap columns, respectively. The second-dimension analysis is performed while switching the trap columns during the first-dimension analysis, so that the number of first-dimension fractions is not limited.

In the present invention, the components separated in the first-dimension analysis columns are successively captured in the two or three trap columns. When the second-dimension analysis of the captured components is finished, a part of the remaining components is eluted from the first-dimension analysis column in the trap columns to be captured. Accordingly, different operations are performed in parallel in the trap columns, including the capture and the second-dimension analysis of partial components, or including the desalting operation in between. Therefore, it is possible to continue the second-dimension analysis with the two or three trap columns without limiting the number of the components. As a result, in the present invention, the system has the less number of the trap columns and a simple structure, thereby making it easy to operate and reducing cost.

When the three trap columns are provided, it is possible to perform the concentrating operation, desalting operation, and eluting operation simultaneously in the different trap columns, respectively, thereby improving productivity.

DETAILED DESCRIPTION OF PREFERRED EMBODIMENTS

Figure 1:
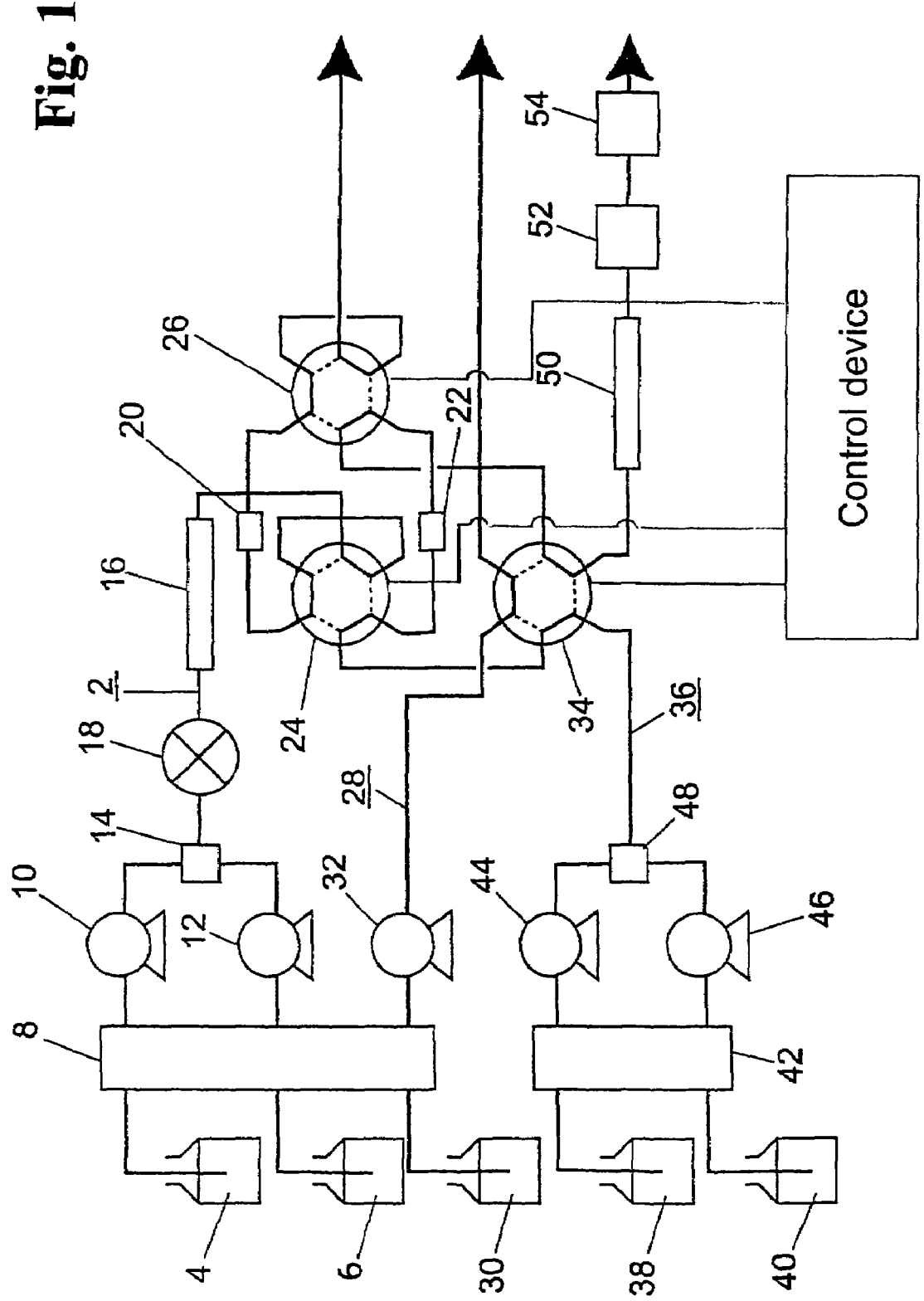
FIG. 1 is a schematic flow diagram of a two-dimensional liquid chromatograph according to a first embodiment of the present invention.

Hereunder, embodiments of the present invention will be explained with reference to the accompanying drawings. FIG. 1 is a schematic flow diagram of a two-dimensional liquid chromatograph according to a first embodiment of the present invention. Reference numeral 2 denotes a first-dimension separation channel. Liquid feed pumps 10 and 12 supply two types of mobile phases 4 and 6 via a degasser 8, and a mixer 14 mixes the mobile phases to be supplied to a first-dimension analysis column 16 for performing gradient elution. An injector 18 is provided between the mixer 14 and the column 16 for injecting a sample. The injector 18 is an auto-sampler so that a sample is injected automatically.

In order to concentrate and capture components separated by the column 16, two trap columns 20 and 22 are connected between two hexahedral valves 24 and 26 for switching the channel, and a downstream side of the column 16 is connected to the valve 24. Reference numeral 28 is a desalting mobile phase channel connected to a hexahedral valve 34 for supplying a desalting mobile phase 30 by a liquid feed pump 32 via the degasser 8. Reference numeral 36 is an analysis channel, and two types of mobile phases 38 and 40 fed by respective liquid delivery pumps 44 and 46 via a degasser 42 are mixed by a mixer 48, and supplied to a second-dimension analysis column 50 via the valve 34 for performing gradient analysis. A UV detector 52 is connected at a downstream side of the column 50 for detecting ultraviolet light absorption, and a mass spectrometer 54 is connected at a further downstream side as a detector.

The channels of the valves 24, 26 and 34 are connected so as to connect the first-dimension separation channel 2 to one trap column 20 (or 22) and to connect the desalting mobile phase channel 28 or the analysis channel 36 to the other trap column 22 (or 20), and also to switch the connections between the trap columns 20 and 22 and the channels 2, 28 and 36. A channel switching mechanism is realized by the valves 24, 26 and 34, and their channel connections.

In the embodiment, a channel is provided for desalting, and when desalting is not performed, the desalting mobile phase channel 28 and the valve 34 become unnecessary. In this case, the channels of the valves 24 and 26 are connected so as to connect the first-dimension separation channel 2 to one trap column 20 (or 22) and to connect the analysis channel 36 to the other trap column 22 (or 20), and also to switch the connections between the trap columns 20 and 22, and the channels 2 and 36.

Figure 2:
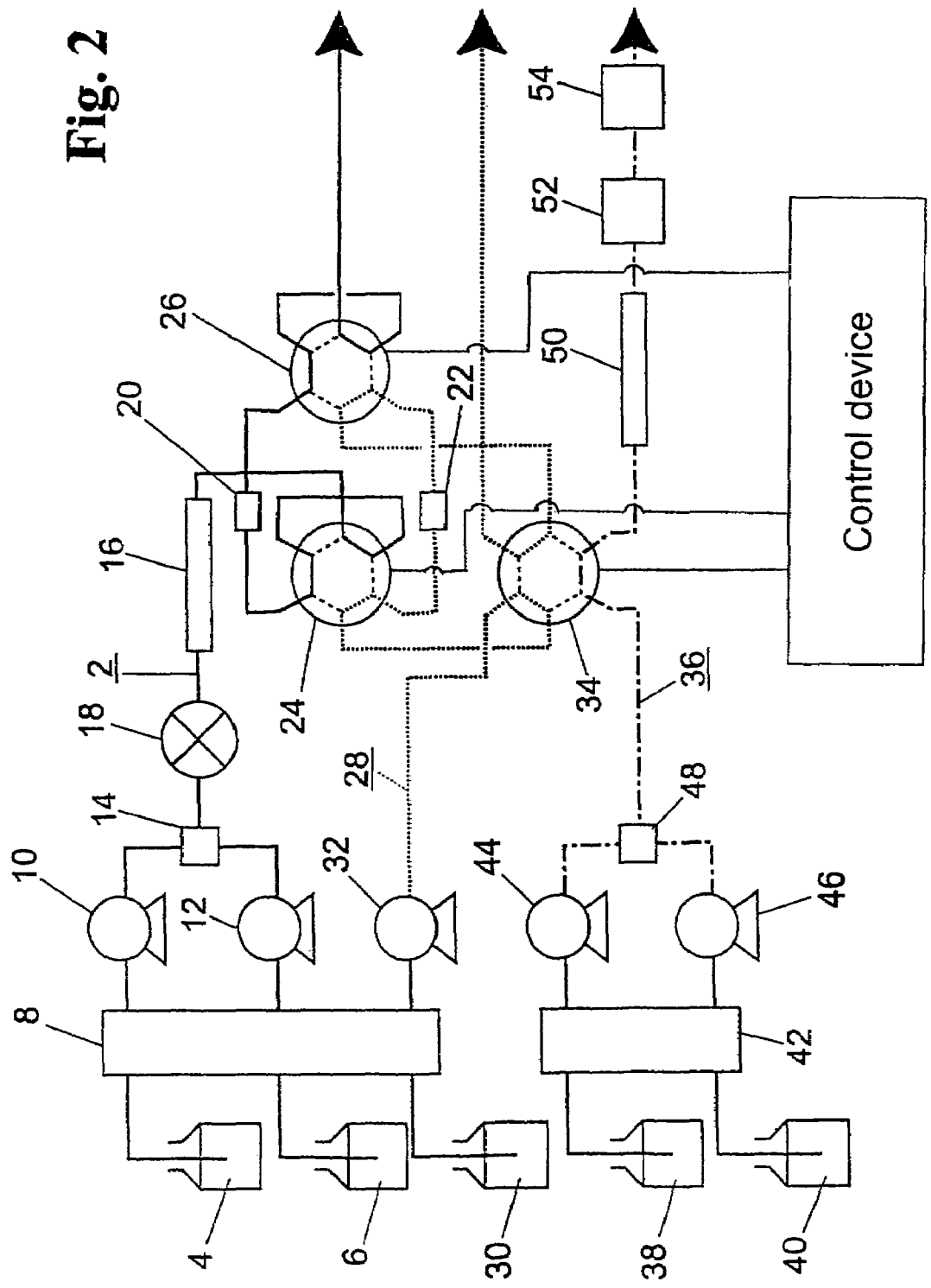
FIG. 2 is a schematic flow diagram of the two-dimensional liquid chromatograph in one operational mode according to the first embodiment.

FIG. 2 is a channel for simultaneously performing a concentrating operation for concentrating components separated in the first-dimension in one trap column, and a desalting operation for performing desalting in the other trap column. Switching of the channels is performed by a control device. By setting of the valves 24, 26 and 34, the component separated in the column 16 is retained in the trap column 20, and the desalting mobile phase is supplied to the component previously retained so that the desalting treatment is performed simultaneously in the trap column 22. In the desalting treatment, the trap column and channels filled with the mobile phase containing salt in the first-dimension analysis is substituted with the desalting mobile phase. In the analysis channel 36, the second-dimension analysis mobile phase is supplied in order to stabilize the column 50.

Figure 3:
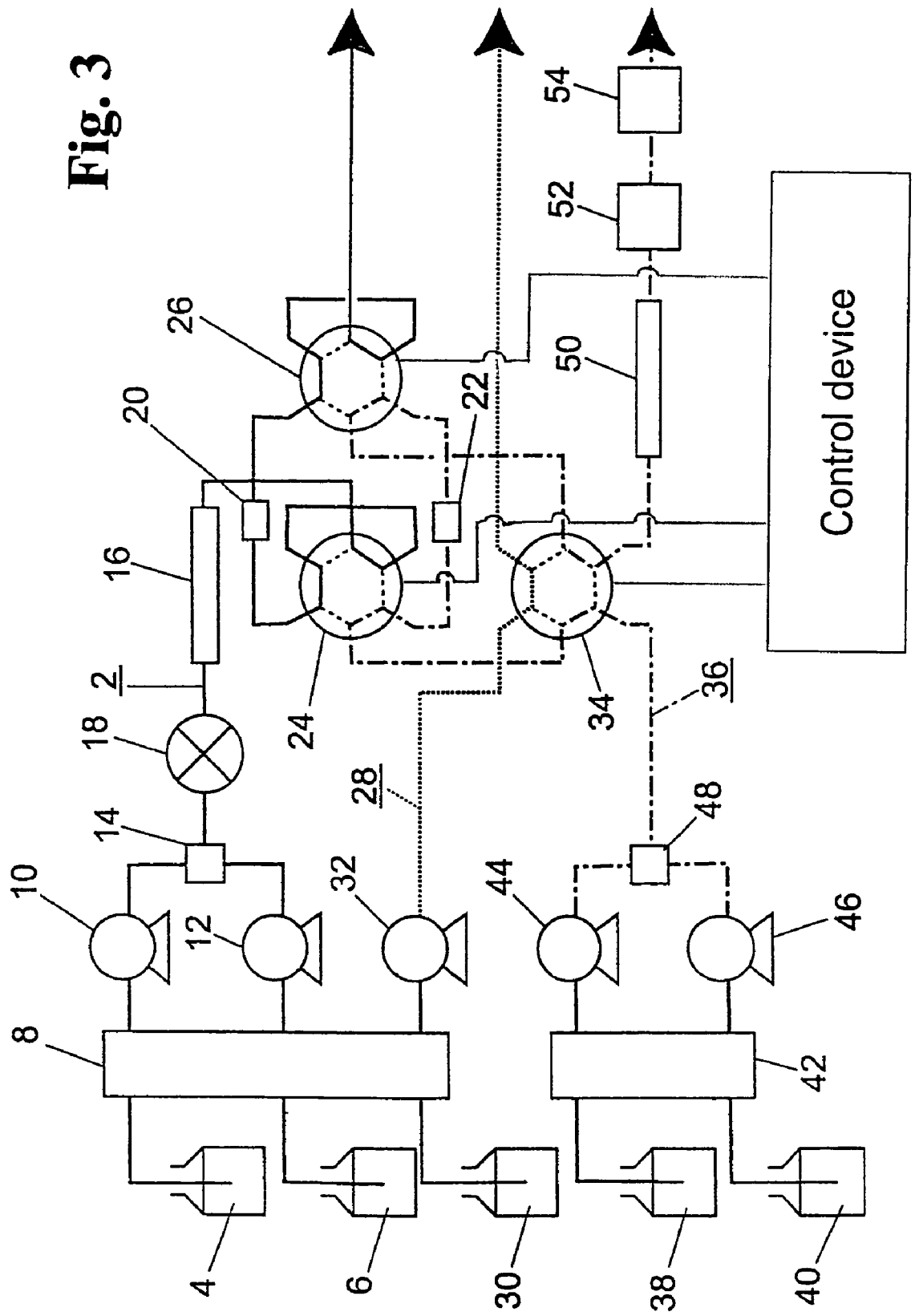
FIG. 3 is a schematic flow diagram of the two-dimensional liquid chromatograph in another operational mode according to the first embodiment.

FIG. 3 is a state in which the valve 34 is switched so as to perform the second-dimension analysis operation for analyzing the component in the trap column after the desalting treatment. The second-dimension analysis mobile phase is supplied to the trap column 22, and the component captured in the trap column 22 is eluted and is sent to the analysis column 50, and separated and detected by the detectors 52 and 54.

When the analysis is finished, the valves 24, 26 and 34 are switched so that desalting treatment of the trap column 20 is performed. The column 16 is connected to the trap column 22, and the component separated in the first-dimension is retained. The components separated in the column 16 successively are retained alternately in the trap columns 20 and 22, and in each trap column 20 and 22, concentration, desalting, and elution are repeated in the order. The channels are switched so that the concentrating operation in one trap column 20 (or 22) and the desalting operation or eluting operation in the other trap column 22 (or 20) are performed simultaneously. Switching of the trap columns 20 and 22 is continued until the first-dimension analysis is finished.

When the desalting is not performed, the concentration and elution are performed in this order in each trap column 20 and 22, and the channels are switched so that the concentrating operation in one trap column 20 (or 22) and the eluting operation in the other trap column 22 (or 20) are performed simultaneously.

Figure 4:
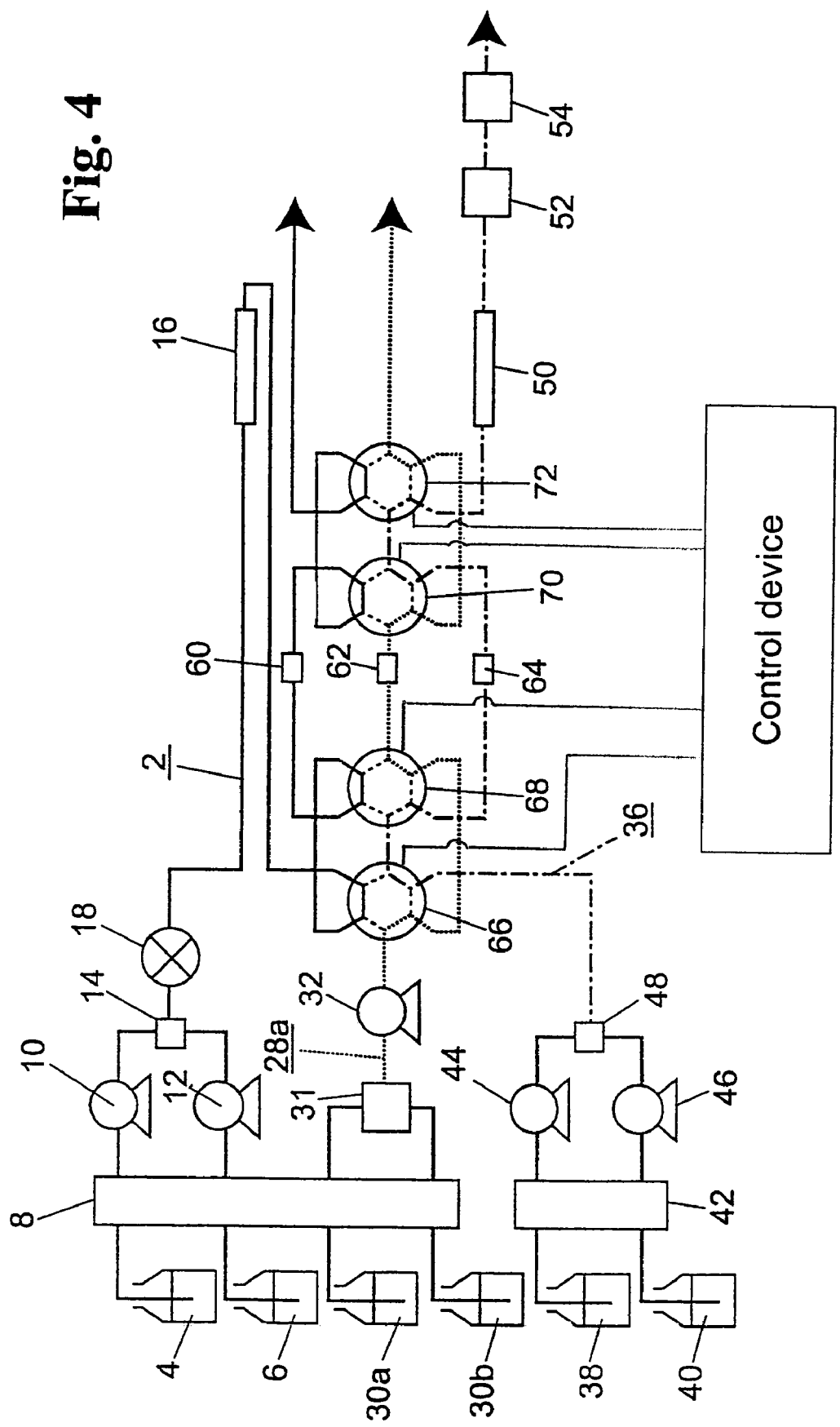
FIG. 4 is a schematic flow diagram of a two-dimensional liquid chromatograph in a first operational mode according to a second embodiment of the present invention.

FIG. 4 is a schematic flow diagram of a two-dimensional liquid chromatograph in a first operational mode according to a second embodiment of the present invention. In the second embodiment, three trap columns are provided, and channels are connected by valves 66, 68, 70 and 72, so that the trap columns 60, 62 and 64 are capable of operating independently.

A downstream side of the column 16 of the first-dimension separation channel 2 is connected to the valve 66, and a desalting mobile phase channel 28a is connected to the valve 66. The desalting mobile phase channel 28a is capable of using two types of solvents in a mixture, and the mobile phases 30a and 30b supplied from a liquid feed pump 32 are mixed by a mixer 31 via a degasser 8. The channel for supplying the second-dimension analysis mobile phase is connected to the valve 66. The channel switching mechanism of the four valves 66, 68, 70 and 72 are connected so that the concentrating operation, desalting operation, and eluting operation can be performed simultaneously in the different trap columns 60, 62 and 64, respectively.

An operation of the second embodiment will be explained. FIG. 4 shows a state in which the channels are connected so that the concentration operation in the trap column 60, the desalting operation in the trap column 62, and the elution operation in the trap column 64 are performed simultaneously.

Figure 5:
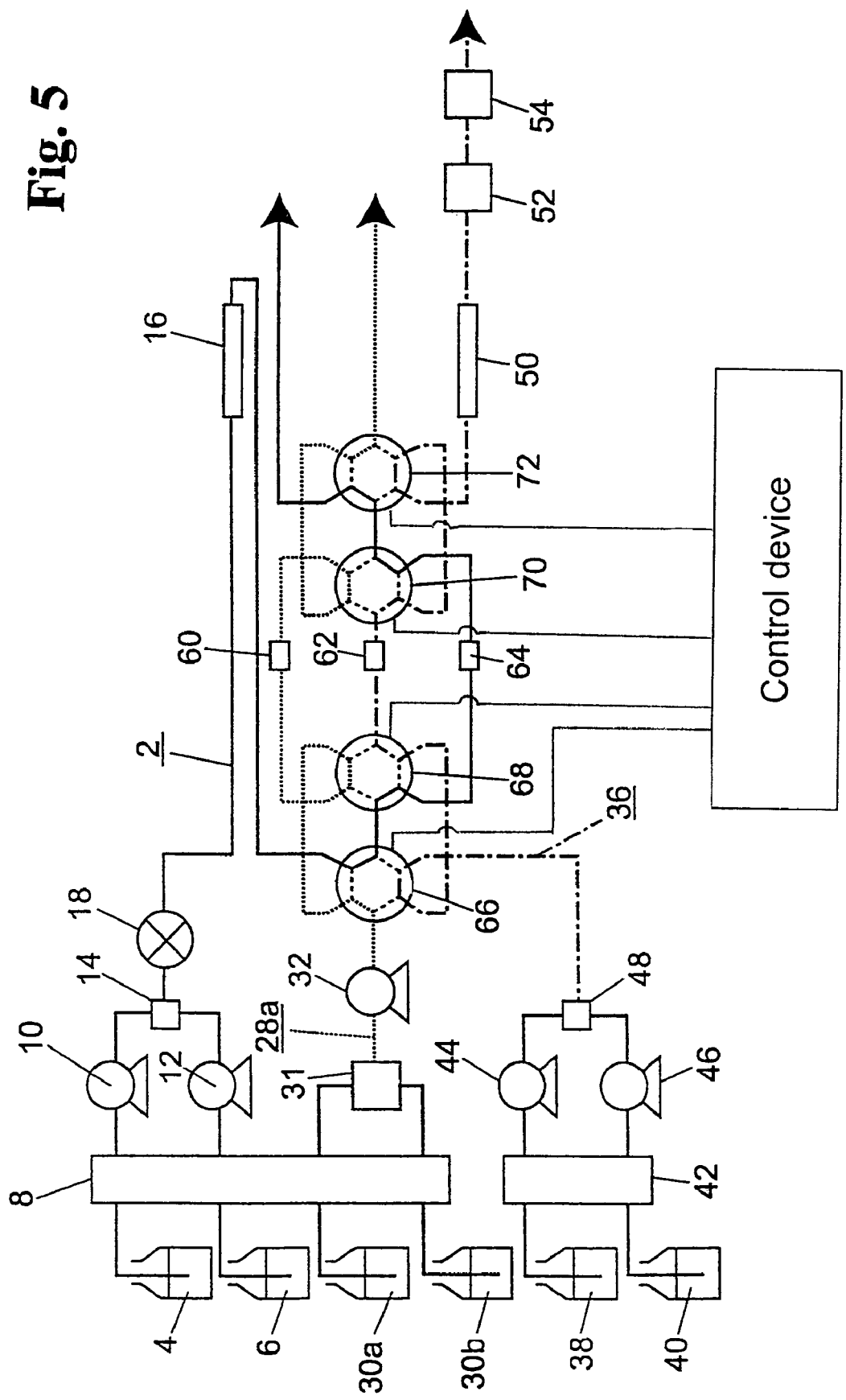
FIG. 5 is a schematic flow diagram of the two-dimensional liquid chromatograph in a second operational mode according to the second embodiment.

FIG. 5 shows a state in which the valves 66, 68, 70 and 72 are switched and the channels are connected, so that the desalting operation in the trap column 60, the elution operation in the trap column 62, and the concentration operation in the trap column 64 are performed simultaneously.

Figure 6:
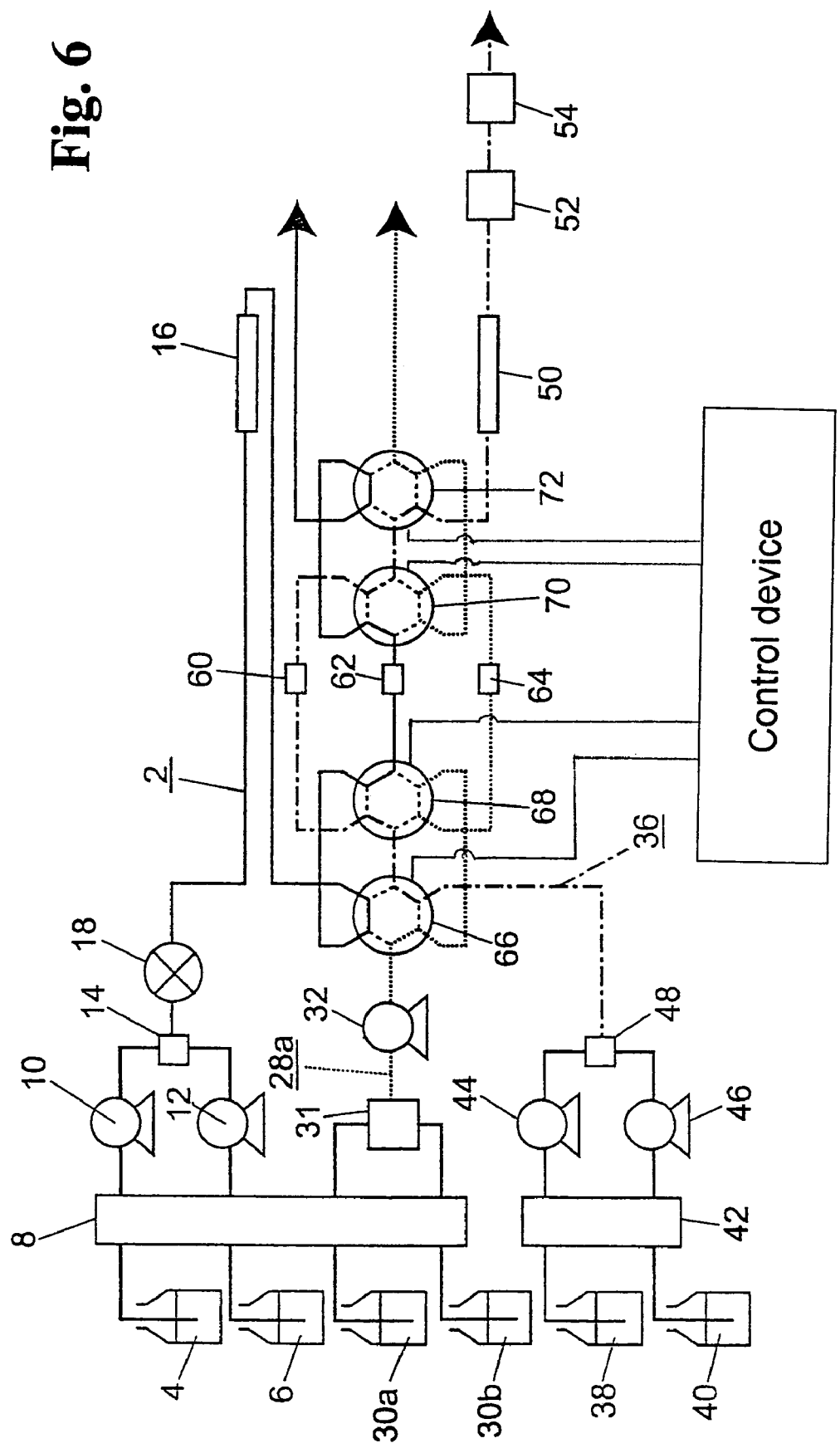
FIG. 6 is a schematic flow diagram of the two-dimensional liquid chromatograph in a third operational mode according to the second embodiment.

FIG. 6 shows a state in which the valves 66, 68, 70 and 72 are switched and the channels are connected, so that the elution operation in the trap column 60, the concentration operation in the trap column 62, and the desalting operation in the trap column 64 are performed simultaneously.

The liquid chromatograph of the present invention is applicable for general chemical analyses including biochemical analysis and biological analysis in fields such as chemistry, biochemistry, medicine, and environment.

The disclosure of Japanese Patent Application No. 2004-097954, filed on Mar. 30, 2004, is incorporated in the application.

While the invention has been explained with reference to the specific embodiments of the invention, the explanation is illustrative and the invention is limited only by the appended claims.

What is claimed is:

1. A two-dimensional liquid chromatograph, comprising:
a sample injection part for injecting a sample,
a first-dimension analysis column for separating the sample,
a first-dimension separation channel for guiding the sample from the sample injection part to the first-dimension analysis column using a first-dimension analysis mobile phase,
a plurality of trap columns respectively connected to the first-dimension analysis column for concentrating components in the sample,
a second-dimension analysis column for analyzing the component in the sample,
an analysis channel for guiding the component in the trap columns to the second-dimension analysis column using a second-dimension analysis mobile phase, a desalting mobile phase channel for supplying a desalting mobile phase to the trap columns, and a channel switching mechanism for switching connections among the trap columns, the first-dimension separation channel, the analysis channel, and the desalting mobile phase channel.

2. A two-dimensional liquid chromatograph according to claim 1, wherein said channel switching mechanism connects one trap column to the first-dimension separation channel, and another trap column to the desalting mobile phase channel or the analysis channel.

3. A two-dimensional liquid chromatograph according to claim 2, wherein three trap columns are provided, and said control device controls the channel switching mechanism so that the concentrating operation, the eluting operation, and the desalting operation are performed simultaneously in the different trap columns.

4. A two-dimensional liquid chromatograph according to claim 1, further comprising a control device for controlling the channel switching mechanism so that each trap column is connected to the first-dimension separation channel for a concentrating operation, to the desalting mobile phase channel for a desalting operation, and to the analysis channel for an eluting operation in this order.

5. A two-dimensional liquid chromatograph according to claim 4, wherein the concentrating operation in one column, and the desalting operation or the eluting operation in another column are performed simultaneously.

* * * * *